United States Patent [19]

Rideout et al.

[11] 4,301,314

[45] Nov. 17, 1981

[54] VAPOR PHASE CHLORINATION OF 1,1-DICHLOROETHANE

[75] Inventors: Walker H. Rideout; Mary E. Jeselnik, both of Corpus Christi, Tex.

[73] Assignee: PPG Industries, Inc., Pittsburgh, Pa.

[21] Appl. No.: 879,029

[22] Filed: Feb. 21, 1978

[51] Int. Cl.³ .............................................. C07C 17/10
[52] U.S. Cl. ..................................... 570/253; 570/255
[58] Field of Search ....................... 260/658 R, 662 R; 570/253, 255

[56] References Cited

U.S. PATENT DOCUMENTS

| 3,012,081 | 12/1961 | Courad et al. | 260/658 R |
| 3,138,643 | 6/1964 | Taylor et al. | 260/658 R |
| 3,304,337 | 2/1967 | Jordan et al. | 260/658 R |
| 3,330,877 | 7/1967 | Kircher et al. | 260/660 |
| 3,449,450 | 6/1969 | Bohl et al. | 260/662 R |
| 3,535,394 | 10/1970 | Pregaglia et al. | 260/658 R |

*Primary Examiner*—Delbert E. Gantz
*Assistant Examiner*—Joseph A. Boska
*Attorney, Agent, or Firm*—Edward J. Whitfield

[57] ABSTRACT

In the preparation of methylchloroform by vapor phase chlorination of 1,1-dichloroethane, the formation of undesirable chlorohydrocarbon reaction products is suppressed by conducting the vapor phase reaction in the presence of a controlled amount of elemental oxygen.

6 Claims, No Drawings

VAPOR PHASE CHLORINATION OF 1,1-DICHLOROETHANE

BACKGROUND OF THE INVENTION

This invention relates to an improvement in the known process for preparing methylchloroform (1,1,1-trichloroethane), a commonly used degreasing solvent, by reacting chlorine and 1,1-dichloroethane in the vapor phase. In addition to methylchloroform, the vapor phase chlorination produces hydrogen chloride, vinylidene chloride, vinyl chloride, unreacted 1,1-dichloroethane, 1,1,2-trichloroethane, 1,2-dichloroethylenes and other higher chlorinated hydrocarbons. Both vinyl chloride and vinylidene chloride may be separated from the reaction mixture and catalytically hydrochlorinated, utilizing the liberated hydrogen chloride, to 1,1-dichloroethane and methylchloroform respectively. The 1,1,-dichloroethane may be recycled to the chlorination feedstock and the methylchloroform may, of course, be combined with the methylchloroform separated from the original reaction mixture.

Since the remaining reaction products, i.e., 1,1,2-trichloroethane, 1,2-dichloroethylenes and higher chlorinated hydrocarbons, are not readily and economically separated or converted to useful products, it is desirable to suppress the formation of these undesirable reaction products. In a typical vapor phase chlorination of 1,1-dichloroethane, it has been found that about 30 or more pounds of these undesirable chlorohydrocarbon reaction products are produced per 100 pounds of methylchloroform product.

Methylchloroform product as used herein refers to the methylchloroform produced directly by the vapor phase chlorination of 1,1-dichloroethane as well as methylchloroform that would be produced were the vinylidene chloride produced by the vapor phase chlorination of 1,1-dichloroethane catalytically hydrochlorinated to methylchloroform.

DESCRIPTION OF THE INVENTION

According to the invention, in the production of methylchloroform by vapor phase chlorination of 1,1-dichloroethane, it has been found that the formation of undesirable chlorohydrocarbon reaction products is suppressed by conducting the vapor phase reaction in the presence of a controlled amount of elemental oxygen. As used herein, the term undesirable chlorohydrocarbon reaction products means chlorohydrocarbon reaction products other than methylchloroform, vinyl chloride and vinylidene chloride. Undesirable chlorohydrocarbon rection products typically produced in the vapor phase chlorination of 1,1-dichloroethane include, for example, 1,1,2-trichloroethane, cis- and trans-1,2-dichloroethylenes, trichloroethylene, perchloroethylene and higher chlorinated hydrocarbons.

Oxygen may be fed directly to the reaction zone of a vapor phase reactor but is preferably fed to the reactor in admixture with the gaseous chlorine and vaporized 1,1-dichloroethane. Gaseous feed mixtures of chlorine and 1,1-dichloroethane containing up to about 600 parts per million (ppm) of elemental oxygen were tested under vapor phase rection conditions and the quantity of undesirable chlorohydrocarbon reaction products produced was found to be significantly less than the vapor phase reaction conducted in the absence of oxygen, reaction conditions being identical in all cases.

Although no precise limits of oxygen concentration have been formulated, it is believed that too high an oxygen concentration might poison the reaction whereas too low an oxygen concentration would not be as beneficial in suppressing the formation of undesirable chlorohydocarbon reaction products.

It is contemplated that under those reaction conditions and reactant ratios at which the vapor phase chlorination of 1,1-dichloroethane is typically carried out, oxygen concentrations useful in the practice of this invention would be in the range of from about 100 to about 600 ppm oxygen, preferably from about 150 to about 500 ppm oxygen and most preferably from about 200 to about 400 ppm oxygen. Although the optimum level of oxygen concentration may vary somewhat depending on reaction conditions and reactant ratios, the same may be readily determined by pre-selecting the desired reaction conditions and reactant ratio and making a series of runs in the presence of measured, incremental amounts of oxygen.

Although elemental oxygen is preferably used according to the invention, the oxygen may be added in the form of atmospheric air.

In accordance with a preferred embodiment of the invention, a gaseous mixture of 1,1-dichloroethane, chlorine and oxygen is introduced into a suitable reactor. The reactor is preferably of the plug flow type, i.e., one in which there is no substantial degree of back mixing between the product gas stream and the feed gas stream. The conditions under which the reaction is conducted may vary over a wide range. The pressure is selected so as to provide optimum contact of the reactant gases with minimum residence time in the reactor. At temperatures below about 350° C., conversion rates are usually undesirably low whereas temperatures above about 550° C. may result in excessive carbonization and product degradation.

The vapor phase reaction is typically conducted at a temperature of between 350° C. and 550° C., preferably from about 400° C. to about 500° C., and at a pressure of up to about 120 psig, preferably from about 40 to 80 psig. Residence time in the reactor is typically from about 0.5 to 5 seconds, preferably from 1 to 2 seconds. The molar ratio of chlorine to 1,1-dichloroethane is typically in the range of from 0.2:1 to 1:1, preferably from about 0.4:1 to 0.8:1.

In a typical practice of the invention, a gaseous mixture of chlorine, 1,1-dichloroethane and oxygen are introduced at a pressure of from 40 to 80 psig to a plug flow reactor maintained at a temperature between 400° C. and 500° C., the residence time of the gaseous mixture in the reactor being about 1 to 2 seconds. The product gas stream from the reactor is passed in known manner through a first separating means, for example, a vacuum distillation column and a first fraction is separated therefrom, said first fraction consisting of hydrogen chloride, vinylidene chloride, vinyl chloride, and trans-1,2-dichloroethylene. The first fraction is hydrochlorinated in known manner in the liquid phase under substantially anhydrous conditions in the presence of a Friedel-Crafts catalyst, such as ferric chloride, to substantially quantitatively convert vinylidene chloride to methylchloroform and vinyl chloride to 1,1-dichloroethane, the hydrogen chloride being consumed in the hydrochlorination reaction with the trans-1,2-dichloroethylene being substantially unaffected. (Alternatively, vinyl chloride may be separated as such prior to hydrochlorination.)

A fraction consisting of 1,1-dichloroethane and cis-1,2-dichloroethylene is separated from the balance of the chlorination product stream and the 1,1-dichloroethane is recycled to the vapor phase chlorination feedstock along with the 1,1-dichloroethane separated from the hydrochlorination product.

Methylchloroform is separated from the balance of the chlorination product and combined with the methylchloroform separated from the hydrochlorination product.

It is apparent that many variations in the foregoing typical process may be made since both vapor phase chlorination of 1,1-dichloroethane as well as liquid phase catalytic hydrochlorination of vinyl chloride and vinylidene chloride are well known processes, the invention residing in conducting the vapor phase chlorination in the presence of a controlled amount of oxygen in order to suppress the formation of undesirable chlorohydrocarbon reaction products.

The invention is further illustrated but is not intended to be limited by the following examples.

EXAMPLE 1

A plug flow type reactor was constructed from a 20 foot (6.1 meters) length of 0.25 inch (6.35 millimeters) outside diameter nickel tube. The tube was formed into a plurality of coils about 6 inches (15.2 centimeters) in diameter. The coiled portion of the tube was positioned in a muffle furnace with the free ends of the tubing protruding through the walls of the furnace. A gaseous mixture of 1,1-dichloroethane and chlorine was continuously introduced under a pressure of 50 psig (4.55 kg/cm$^2$) into one end of the tube, the normally liquid 1,1-dichloroethane having first been vaporized in a preheater. The molar ratio of chlorine to 1,1-dichloroethane was 0.7 to 1. The gaseous mixture was passed through the coiled portion of the tube that had been preheated and stabilized at the reaction temperature of 450° C., the residence time of the gaseous mixture in the reaction being about 1 second. The product gas stream was withdrawn from the other end of the tube, passed through a scrubbing train, collected and analyzed. The analytical results are summarized in Table I.

EXAMPLES 2 to 6

The procedure described in Example 1 was followed except that measured incremental amounts of elemental oxygen were added to the gaseous feed mixture. Five runs were made under the reaction conditions specified in Example 1 at a molar ratio of chlorine to 1,1-dichloroethane of 0.7 to 1 maintaining oxygen concentrations in the feed gas mixture of 150, 300, 300, 450 and 600 ppm, respectively. Analyses of the respective product gas streams are summarized in Table I.

From an inspection of the data, it is readily seen that when 1,1-dichloroethane is chlorinated in the vapor phase in the presence of controlled relatively small amounts of elemental oxygen, the same results in a substantial reduction in the quantity of undesirable halohydrocarbon reaction products as compared with the vapor phase chlorination of 1,1-dichloroethane conducted in the absence of oxygen under identical reaction conditions. In addition, the yield of methylchloroform is substantially increased.

Although the invention has been described with specific references to and specific details of embodiments thereof, it is to be understood that it is not intended to be so limited since changes and alterations therein may be made which are within the full intended scope of this invention as defined by the appended claims.

TABLE I

Vapor Phase Chlorination of 1,1-Dichloroethane Effect of Oxygen Concentration on Suppression of the Formation of Undesirable Chlorohydrocarbon Reaction Products

| Example | 1 | 2 | 3 | 4 | 5 | 6 |
|---|---|---|---|---|---|---|
| Oxygen in feed, ppm | 0 | 150 | 300 | 300 | 450 | 600 |
| Reaction products, mole percent: | | | | | | |
| Vinyl chloride | 26.1 | 23.4 | 24.1 | 23.8 | 18.8 | 23.1 |
| 1,1-Dichloroethane | 8.1 | 4.9 | 4.7 | 5.8 | 3.2 | 5.4 |
| Vinylidene chloride | 46.2 | 37.5 | 34.0 | 27.8 | 45.7 | 35.5 |
| Methylchloroform | 4.9 | 24.0 | 27.9 | 32.8 | 21.8 | 24.7 |
| 1,1,2-Trichloroethane | 2.0 | 0.9 | 1.1 | 1.2 | 0.8 | 1.7 |
| cis-1,2-Dichloroethylene | 2.8 | 2.5 | 2.3 | 2.2 | 2.0 | 2.6 |
| trans-1,2-Dichloroethylene | 2.4 | 2.2 | 2.2 | 1.7 | 1.9 | 2.3 |
| Tetrachloroethane | 2.6 | 1.3 | 1.1 | 1.5 | 1.5 | 1.6 |
| Trichloroethylene | 3.8 | 2.2 | 1.6 | 2.0 | 2.8 | 1.9 |
| Perchloroethylene | 0.1 | <0.1 | 0.1 | 0.3 | <0.1 | 0.1 |
| Pentachloroethane | — | <0.1 | — | <0.1 | <0.1 | — |
| Carbon tetrachloride | <0.1 | <0.1 | <0.1 | — | <0.1 | — |
| Unknown | 1.0 | 1.0 | 0.8 | 0.7 | 1.3 | 1.1 |
| Pounds UCRP* 100 pounds MC** | 27.7 | 16.2 | 14.5 | 15.2 | 15.6 | 18.5 |

*UCRP - Undesirable chlorohydrocarbon reaction products, i.e., those chlorohydrocarbons other than vinyl chloride, unreacted 1,1-dichloroethane, vinylidene chloride and methylchloroform.
**MC - Methylchloroform; includes both methylchloroform directly produced by the vapor phase chlorination as well as methylchloroform that would be produced were the vinylidene chloride completely converted to methylchloroform by liquid phase catalytic hydrochlorination.

We claim:
1. In a process for the production of the methylchloroform wherein chlorine and 1,1-dichloroethane are reacted under conditions of temperature and pressure sufficient to maintain the reactants in the vapor phase, the improvement comprising conducting said vapor phase reaction between chlorine and 1,1-dichloroethane in the presence or a controlled quantity of elemental oxygen in amounts of up to about 600 parts per million parts of chlorine and 1,1,-dichloroethane to obtain a reaction product having a higher mole percentage of methylchloroform than that obtained were the reaction conducted in the absence of oxygen uner the same conditions of temperature and pressure, and at the same reactants ratio.
2. The improvement of claim 1 wherein oxygen is present in an amount of from about 100 to about 500 parts per million.
3. The improvement of claim 2 wherein oxygen is present in an amount of from about 200 to about 400 parts per million.
4. In a process for the production of methylchloroform comprising feeding of vaporous feed mixture of chlorine and 1,1-dichloroethane to a plug flow reactor and reacting vaporous mixture therein at a temperature and pressure sufficient to maintain the reactants in the vapor phase, the improvement comprising adding a controlled amount of oxygen to the reactor feed mixture and maintaining an oxygen concentration in the feed mixture of up to about 600 parts per million parts of feed mixture to obtain a reaction product having a higher mole percentage of methylchloroform than that obtained where the reaction conducted in the absence of oxygen under the same conditions of temperature and pressure and at the same reactants ratio.
5. The improvement of claim 4 wherein the oxygen content of the feed mixture is maintained in the range of from about 100 to about 500 parts per million.
6. The improvement of claim 5 wherein the oxygen content of the feed mixture is maintained in the range of from about 200 to about 400 parts per million.

* * * * *

UNITED STATES PATENT AND TRADEMARK OFFICE
CERTIFICATE OF CORRECTION

PATENT NO. : 4,301,314
DATED : November 17, 1981
INVENTOR(S) : Walker H. Rideout; Mary E. Jeselnik It is certified that error appears in the above-identified patent and that said Letters Patent are hereby corrected as shown below:

In Claim 1, column 4, line 36, "in the presence or" should read --in the presence of--.

In Claim 1, column 4, line 41, "uner" should read --under--.

Signed and Sealed this

Ninth Day of February 1982

[SEAL]

Attest:

GERALD J. MOSSINGHOFF

*Attesting Officer*   *Commissioner of Patents and Trademarks*